United States Patent [19]  [11] 4,088,703
Yeh et al.  [45] May 9, 1978

[54] RECOVERY OF PHENOL VALUES FROM PURIFICATION RESIDUES

[75] Inventors: Chuen Y. Yeh, Succasunna; F. Lewis Bohn; Harry E. Ulmer, both of Morristown, all of N.J.

[73] Assignee: Allied Chemical Corporation, Morris Township, N.J.

[21] Appl. No.: 407,712

[22] Filed: Oct. 18, 1973

[51] Int. Cl.² ............................................. C07C 35/08
[52] U.S. Cl. ..................................................... 568/835
[58] Field of Search ..................................... 260/631 H

[56] References Cited

U.S. PATENT DOCUMENTS

| | | | |
|---|---|---|---|
| 1,696,782 | 12/1928 | Schoeller et al. | 260/631 H |
| 1,787,205 | 12/1930 | Laehr | 260/618 H |
| 2,829,166 | 4/1974 | Joris et al. | 260/631 H |

Primary Examiner—Donald G. Daus
Assistant Examiner—D. P. Springer
Attorney, Agent, or Firm—Jay P. Friedenson; Jack B. Murray

[57] ABSTRACT

Processes for the recovery of phenol values as cyclohexanol from the purification residue obtained in the amine purification of phenol. The recovery of phenol values may be effected by hydrogenation in the presence of a nickel catalyst and distilling the hydrogenation product to obtain cyclohexanol. Alternatively, the purification residue may be distilled and the distillate hydrogenated to produce a hydrogenation product from which cyclohexanol may be recovered by a second distillation.

10 Claims, 1 Drawing Figure

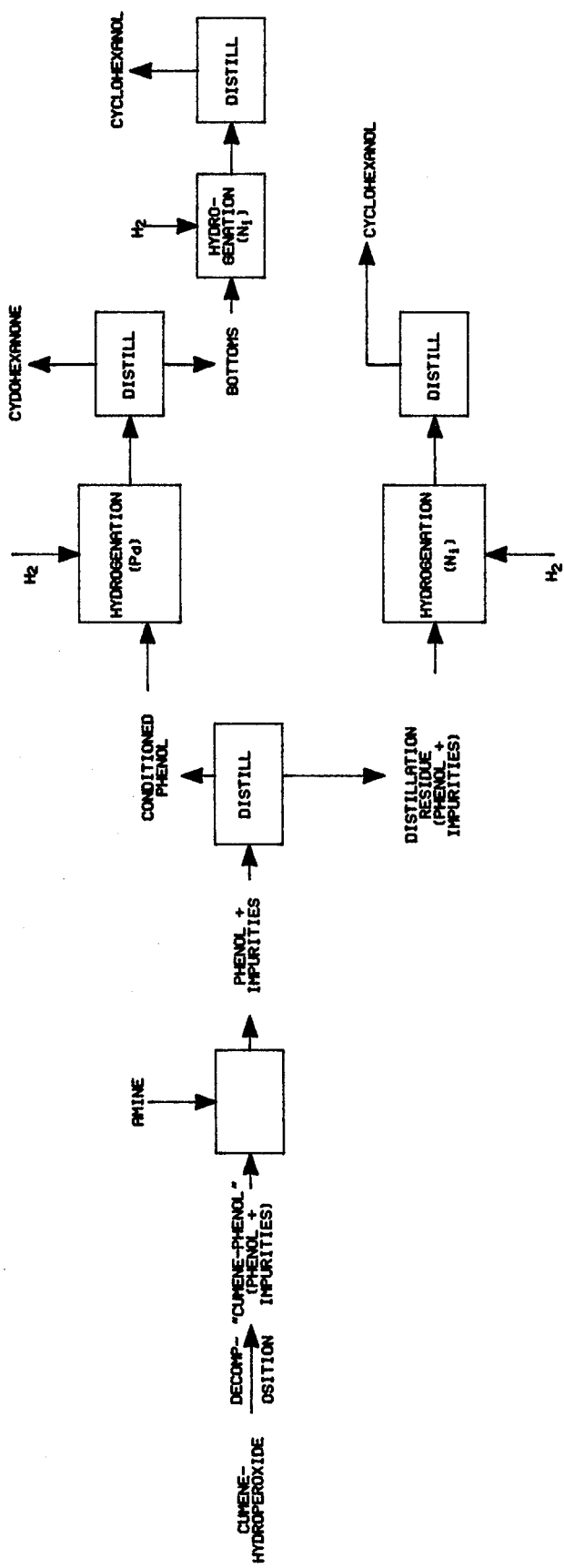

RECOVERY OF PHENOL VALUES FROM PURIFICATION RESIDUES

BACKGROUND OF THE INVENTION

1. Field of the Invention

This invention relates to the recovery of phenol values as cyclohexanol from a purification residue and more particularly to the recovery of phenol values as cyclohexanol from the purification residue obtained in the amine purification of phenol.

2. Description of the Prior Art

The production of cumene-phenol, i.e., phenol produced by the oxidation of cumene and the decomposition of the resulting hydroperoxide in the presence of an acidic catalyst, is well known in the art. While such phenol is satisfactory for many purposes, where it is desired to reduce this phenol to cyclohexanone, it is necessary to purify the phenol to remove impurities detrimental to reduction. Such a purification, which is herein termed "amine purification of phenol," may be performed by a variety of methods, all of which involve the addition to the phenol of an amine in order to remove carbonyl impurities from the phenol. Examples of amine purification may be found in U.S. Pat. No. 3,322,651 wherein nitrogen compounds such as ammonia, alkyl amine, dialkyl amine and aralkyl amine are employed; U.S. Pat. No. 3,692,845 wherein a polyamine such as hexamethylenediamine or hexamethylenetriamine are employed; and U.S. Pat. No. 3,187,050 wherein the trisodium salt of ethylenediaminetetraacetic acid and sodium hydroxide are employed to treat the phenol. In addition, the amine purification of phenol may be effected by a combination of the processes disclosed in the above patents, e.g. cumene-phenol may be treated with a mixture of hexamethylenediamine and the trisodium salt of ethylenediaminetetraacetic acid. Generally, after addition of the selected amine to the cumene-phenol, the mixture is distilled to produce phenol as distillate.

While these amine purification processes produce a relatively pure phenol as distillate, they have the disadvantage of producing as distillation bottoms a residue, herein referred to as the "purification residue," which contains from about 40 to 65 percent by weight phenol, in addition to impurities such as imines of acetone, acetophenone, acetol and mesityloxide together with alpha methylstyrene, methylbenzofuran, heavy metals, sodium phenate and other unknown impurities, in addition to unreacted treating agents. Since discarding this purification residue would effect a severe economic penalty, it is desirable to recover phenol values from the purification residue. While such a residue can be subjected to further distillation in order to effect removal of phenol, the phenol thus obtained contains an unacceptable amount of impurities carried over from the purification residue. The impurities present in the phenol thus obtained are heavy metals, including nickel, iron, copper, lead, zinc, cobalt, tin and chromium, silica, halogens, acetone, alpha methylstyrene, methylbenzofuran and unknowns. Of the foregoing impurities present in the phenol, acetone and halogens are known to inhibit hydrogenation reactions of phenol. In addition, impurities such as iron, copper, zinc, and tin present in the phenol are known to poison hydrogenation catalysts and thereby necessitate frequent regeneration of the catalysts. Thus, phenol distilled from the purification residue is not suitable, for example, for hydrogenation to cyclohexanone.

SUMMARY OF THE INVENTION

By the processes of the present invention, the purification residue obtained in the amine purification of phenol is treated to recover phenol values as cyclohexanol. According to one embodiment of the present invention, the purification residue is hydrogenated in the presence of a nickel catalyst to produce a hydrogenation product from which cyclohexanol is recovered by distillation. The distillate thereby obtained is relatively pure cyclohexanol containing less than about 2.0 weight percent impurities. In addition, hydrogenation of the purification residue in the presence of a nickel catalyst has been surprisingly found to effect a conversion to cyclohexanol of at least about 95%, despite the presence in the residue of the impurities which are known to be inhibitors of the hydrogenation reaction. In addition, hydrogenation of this residue produces cyclohexanol without significant poisoning of the catalyst despite the presence in the residue of impurities which are known to poison hydrogenation catalysts.

A second embodiment of the present invention comprises distilling the purification residue to recover phenol containing impurities and hydrogenating the phenol in the presence of a nickel catalyst to produce a hydrogenation product from which relatively pure cyclohexanol may be recovered by a second distillation. In this embodiment of the invention it has also been unexpectedly found that while the phenol obtained by distillation of the purification residue contains as much as 2000 ppm of impurities, such as those mentioned above, high conversions to relatively pure cyclohexanol are obtained and the nickel catalyst remains substantially unaffected by those impurities.

Thus the process of the present invention surprisingly produces high conversions of relatively pure phenol from the purification residue obtained in the amine purification of phenol and thereby avoids the severe economic penalty resulting from discarding the purification residue. Further, the nickel catalyst employed in the hydrogenation step has been found to be substantially unaffected by the impurities present in the residue and may be used for long periods of time without regeneration.

DETAILED DESCRIPTION OF THE INVENTION

According to the process of the present invention, phenol values are recovered as cyclohexanol from the purification residue, obtained in the amine purification of phenol, by hydrogenating the residue in the presence of a nickel catalyst and distilling the hydrogenation product to recover relatively pure cyclohexanol therefrom. As used herein the term "relatively pure cyclohexanol" is meant to define cyclohexanol having not more than about 2.0 weight percent impurities. The purification residue generally contains from about 40 to about 65 weight percent phenol and, correspondingly, from about 35 to 60 weight percent impurities. These impurities may include imines of acetone, acetol, mesityloxide and aceptophenone together with heavy metals, amines (e.g. ammonia, alkyl amine, trisodium salt of ethylenediaminetetraacetic acid, hexamethylenetriamine or hexamethylenediamine), alpha methylstyrene, methylbenzofuran and other unknown impurities together with unreacted heating agents.

The purification residue may be itself hydrogenated to produce a hydrogenation product from which relatively pure cyclohexanol may be obtained by distillation. Alternatively, the purification residue may be first distilled to produce a distillate, herein termed the "purification residue distillate" containing phenol and impurities which is then hydrogenated and relatively pure cyclohexanol recovered from the hydrogenation product by a second distillation. Thus, the term "mixture to be hydrogenated" as used herein is meant to define either the purification residue or the purification residue distillate.

The hydrogenation of phenol to produce cyclohexanol proceeds by a reaction which may be illustrated by the following equation:

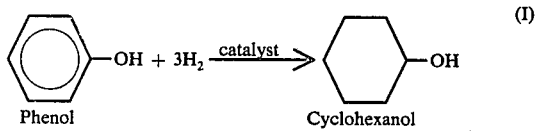

Distillation of the hydrogenation product conveniently separates the product cyclohexanol from other constituents of the hydrogenation product, such as cyclohexanone, which may also be produced by the hydrogenation of phenol as may be illustrated by the following equation:

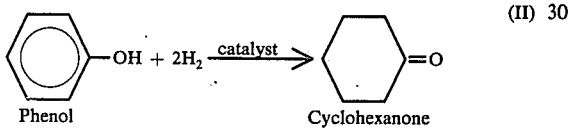

The amount of cyclohexanone formed during hydrogenation of either the purification residue or the purification residue distillate by the processes of this invention is generally from about 1.0 to 2.0 weight percent of the hydrogenation product. It has been found that during hydrogenation with a nickel catalyst the concentration of cyclohexanone in the hydrogenation product does not appreciably vary with the phenol content of the mixture to be hydrogenated or with either temperature or pressure conditions of hydrogenation.

The hydrogenation step of the process of the present invention may be performed in any of the conventional apparatus, e.g. Magne-Drive autoclave, employed for the hydrogenation of phenol at elevated temperature and pressure.

Whether the hydrogenation is performed upon the purification residue distillate or the purification residue itself, in either case hydrogenation is generally performed at a pressure of from about 60 to 200 psig with a pressure of from about 90 to 150 psig being preferred. The temperature of the hydrogenation step may be from 40° to 260° C. and preferably is from about 100° to 200° C. Pressures greater than 200 psig may be employed where the hydrogenation apparatus can withstand such greater pressures.

In the hydrogenation step of the process of the present invention, any nickel catalyst may be employed, with Raney nickel catalyst, commercially available as an aqueous suspension containing approximately 50 weight percent Raney nickel, being preferred. Adkins nickel catalyst is also suitable. The selected nickel catalyst may be employed in any concentration greater than about one percent by weight and is preferably employed in a concentration of from about one to ten percent by weight of the mixture to be hydrogenated. While larger concentrations may be employed, a catalyst concentration of greater than about ten percent by weight does not effect a significantly greater conversion of phenol to cyclohexanol, and use of less than about one percent by weight catalyst generally results in undesirably low cyclohexanol conversion. Sodium carbonate, or sodium hydroxide may be additionally added as promoters to the mixture to be hydrogenated. While the amount of such promoter added is not critical, the concentration of the promoter will generally be from about 0.01 to 0.50 percent by weight of the mixture to be hydrogenated in order to enhance the rate of reaction during hydrogenation. Other suitable promoters are potassium carbonate and calcium carbonate. The use of the above promoters may reduce the time of hydrogenation by as much as 75%.

The hydrogenation gas employed in the process of the present invention preferably contains hydrogen in concentrations of at least 60 percent by volume and may additionally contain an inert gas such as nitrogen in concentrations of up to about 40 percent by volume. The hydrogenation gas preferably does not contain gases other than hydrogen which are reactive with any constituent of the purification residue so as to avoid reactions which compete with the desired hydrogenation reaction. Hydrogen may be introduced continually into the hydrogenation apparatus during hydrogenation to replace that portion which has reacted. Alternatively, hydrogen may be reacted batchwise with incremental additions made when that hydrogen initially added has reacted.

In the hydrogenation step, flushing of the hydrogenation apparatus in order to eliminate oxygen, thereby avoiding oxidation of constituents of the mixture to be hydrogenated, should be performed prior to hydrogenation. Flushing is necessary after each introduction of air into the chamber which may occur, as for example, following the removal of hydrogenation product from the chamber. While any gas which is not reactive with the constituents of the mixture to be hydrogenated may be employed, the preferred flushing gas is nitrogen.

The period of time required for maximum conversion of phenol by hydrogenation to cyclohexanol varies depending upon the temperature and pressure, the concentration of catalyst, promoter and phenol present in the mixture to be hydrogenated, and the volume of the mixture subjected to hydrogenation. The period of time for which the hydrogenation to proceed is at least about one hour and preferably from about 2 to 4 hours.

Following hydrogenation, distillation of the hydrogenation product to produce a distillate containing relatively pure cyclohexanol is generally performed at a temperature of from about 90° to 180° C. and preferably from about 110° to 150° C. Where in the first instance the purification residue is distilled to produce a distillate which is then subjected to hydrogenation, the purification residue is distilled at a temperature of from about 90° to 190° C. and preferably from about 100° to 150° C. The apparatus to be employed in the above distillations may be any conventional equipment employed for the distillation of similar fluids under similar temperature conditions.

The purification residue normally exhibits a high viscosity which ranges from about 5 cps at 167° C. to about 100 cps at 52° C. In order to provide ease of handling of such residue, the purification residue may therefore be heated to at least about 75° C. in order to effect an increase in its viscosity. Alternatively, the residue may be mixed with either pure phenol or with a less viscous fluid whose constituents are not reactive with the constituents of the residue. While the proportions of phenol or other liquid to be mixed with the residue are not critical, it is preferred that about 1 part by volume of such less viscous liquid be employed for every two parts by volume of purification residue.

Since the presence of water in the material to be hydrogenated decreases the rate of hydrogenation, it is desirable that any excess water present be removed prior to hydrogenation. Removal of water may be effected by distillation. While less preferred, water may also be removed by adsorption of the water by passing the mixture to be hydrogenated through a bed of molecular sieve 4A or other suitable adsorbing materials. The selected process for removing water should remove sufficient water so as to produce a mixture to be hydrogenated containing not greater than about 2 weight percent water and preferably not greater than about 1 weight percent.

Recovery of catalyst from the hydrogenation product may be effected by any of several means, such as by centrifuging, filtering or allowing the catalyst to settle and decanting the liquid and then recycling the solids to the hydrogenation chamber for subsequent hydrogenation. Make-up catalyst may, of course, be added to the hydrogenation chamber in the event that some catalyst is lost during the catalyst recovery step.

Following the removal by distillation of product cyclohexanol from the hydrogenation product, a distillation bottoms remains which may be either discarded or combined with combustible liquids to be burned as fuel, thereby taking advantage of the combustible characteristics of the distilled bottoms in providing an energy source.

A relatively pure cyclohexanol obtained by the process of present invention is suitable for use in the systhesis of adipic acid used in the manufacture of nylon.

The process of the present invention may be further illustrated by reference to the following examples in which parts are by weight:

EXAMPLE 1

To 160 parts of purification residue, obtained in the amine purification of cumene-phenol (wherein the phenol was heated in the presence of hexamethylenetriamine and the trisodium salt of ethylenediaminetetraacetic acid and then distilled) and containing 60.5 weight percent phenol and 39.5 weight percent impurities consisting of imines of acetone, acetol, mesityloxide, and acetophenone, alpha methylstyrene, methylbenzofuran, acetylene, sodium phenate, hexamethylenetriamine, halogens, silica, heavy metals and unknowns, is added 0.15 part sodium carbonate together with eight parts of a solution containing 4 parts Raney nickel catalyst in 4 parts of water. This mixture is introduced into a Magne-Drive autoclave. The autoclave is purged three times by introducing gaseous nitrogen into the autoclave at a pressure of 60 psig and bleeding the pressure down to 5 psig. The same purging procedure is repeated with hydrogen. Hydrogen pressure is then adjusted to 100 psig and the temperature in the autoclave raised to 180° C. A pressure of 100 psig and a temperature of 180° C. is maintained throughout the reaction.

At the conclusion of three hours of operation, the hydrogenation product is withdrawn and subjected to distillation in a conventional distillation column at a temperature of 115° C., and 95 parts of cyclohexanol are obtained as distillate, thereby effecting 98% conversion of phenol to cyclohexanol. The cyclohexanol so obtained is determined to contain only 1 weight percent impurities.

EXAMPLE 2

To a mixture of 104 parts of purification residue, obtained as in Example 1, together with 56 parts of phenol is added 0.10 parts of sodium carbonate together with 8 parts of a solution containing 4 parts of Raney nickel catalyst in 4 parts of water. This mixture is introduced into a Magne-Drive autoclave. The autoclave is purged three times by introducing the gaseous nitrogen into the autoclave at a pressure of 50 psig and bleeding the pressure down to 5 psig. The same purging procedure is repeated with hydrogen. Hydrogen pressure is then adjusted to 100 psig and the temperature raised in the autoclave to 180° C. A pressure of 100 psig and a temperature of 180° C. is maintained in the autoclave for a period of four hours. At the end of the four hour period, the hydrogenation product is removed from the autoclave and the catalyst is removed by filtration and recycled for hydrogenation of a second mixture containing purification residue.

Six successive hydrogenations are performed employing recycled catalyst, each hydrogenation effecting a hydrogenation product from which 109 parts cyclohexanol and 2 parts cyclohexanone, corresponding to about 92 percent converstion of phenol to cyclohexanol, are recovered by distillation. Cyclohexanol of commercial purity, i.e. containing less than about 2 weight percent impurities, is obtained by distillation of each hydrogenation product. At the end of the sixth hydrogenation, no significant catalyst poisoning is observed.

EXAMPLE 3

368 Parts of the purification residue, obtained as in Example 1, are distilled at a temperature of 115° C. in a ten theoretical plate Snyder column. After an initial 6% fraction consisting primarily of water is discarded, a 55% fraction containing 335 parts of phenol is collected. An analysis of the phenol fraction reveals that the following impurities are present.

| Impurity | Concentration (ppm) |
|---|---|
| Acetone | 35 |
| Methylbenzofuran | 29 |
| Alpha-Methylstyrene | 4 |
| Halogens | 2 |
| Nickel | 5 |
| Silica | 2 |
| Iron | 1 |
| Copper | 0.4 |
| Zinc | 0.4 |
| Cobalt | 0.4 |
| Aluminum | 0.3 |
| Tin | 0.3 |
| Chromium | 0.3 |
| Lead | 0.2 |
| Unknowns | 4 |

163 Parts of the phenol fraction are charged to a Magne-Drive autoclave and 0.10 part of sodium carbonate together with 8 parts of a solution containing 4 parts Raney nickel catalyst in four parts of water are added. The autoclave is purged three times by introducing gaseous nitrogen into the autoclave at a pressure of 50 psig and bleeding the pressure down to 5 psig. The same purging procedure is repeated with hydrogen. Hydrogen pressure is then adjusted to 100 psig and the temperature raised in the autoclave to 180° C. A pressure of 100 psig and a temperature of 180° C. is maintained in the autoclave for a period of two hours. At the end of the 2 hour period the hydrogenation product is removed from the autoclave and the catalyst is separated from the mixture by filtration and recycled for hydrogenation of a second mixture containing phenol fraction.

Following separation of the catalyst from the hydrogenation product, the hydrogenation product is distilled at a temperature of 115° C. to yield a distillate containing 1 part of cyclohexanone and 160 parts of relatively pure cyclohexanol, i.e. containing less than about 1% impurities. Thus, 98% of theoretical conversion of phenol to cyclohexanol is effected.

Six successive hydrogenations are performed employing recycled catalyst, each hydrogenation effecting a high conversion (at least about 95%) of phenol to cyclohexanol in the hydrogenation product, from which cyclohexanol of commercial purity is obtained by subsequent distillation. At the end of the sixth hydrogenation, no significant catalyst poisoning is observed.

We claim:

1. A process for recovering phenol values as cyclohexanol from the purification residue obtained by the amine purification of cumene-phenol which comprises the steps of:
   (a) hydrogenating said purification residue at a temperature of from about 40° to 260° C. in the presence of nickel catalyst to produce a hydrogenation product containing cyclohexanol, said catalyst being present in an amount greater than about 1 percent by weight of said purification residue, and
   (b) distilling said hydrogenation product to recover cyclohexanol therefrom.

2. The process according to claim 1 wherein said nickel catalyst is Raney nickel catalyst and wherein said purification residue contains at least one impurity selected from the group consisting of alpha-methylstyrene, methylbenzofuran, heavy metals, sodium phenate, and imines of acetone, acetophenone, acetol and mesityloxide.

3. The process according to claim 1 wherein said nickel catalyst is employed in a concentration of from about 1 to 10 percent by weight of the purification residue.

4. The process according to claim 1 wherein a promoter selected from the group consisting of sodium hydroxide, sodium carbonate, potassium carbonate and calcium carbonate is incorporated in the purification residue.

5. The process according to claim 1 wherein said hydrogention is performed at a pressure of from about 60 to 200 psig for a period of at least about 1 hour.

6. A process for recovering phenol values as cyclohexanol from the purification residue obtained by the amine purification of cumene-phenol which comprises the steps of:
   (a) distilling said purification residue to recover phenol containing impurities as purification residue distillate;
   (b) hydrogenating said purification residue distillate at a temperature of from about 40° to 260° C. in the presence of nickel catalyst to produce a hydrogenation product containing cyclohexanol, said catalyst being present in an amount greater than about 1 percent by weight of said purification residue distillate; and
   (c) distilling said hydrogenation product to recover cyclohexanol therefrom.

7. A process according to claim 6 wherein said nickel catalyst is Raney nickel catalyst and wherein said purification residue contains at least one impurity selected from the group consisting of alphs-methylstyrene, methylbenzofuran, heavy metals, sodium phenate and imines of acetone, acetophenone, acetol or mesityloxide.

8. The process according to claim 6 wherein said nickel catalyst is employed in a concentration of from about 1 to 10 percent by weight of the purification residue distillate.

9. The process according to claim 6 wherein a promoter selected from the group consisting of sodium hydroxide, sodium carbonate, potassium carbonate and calcium carbonate is incorporated in the purification residue.

10. The process according to claim 6 wherein said hydrogenation is performed at a pressure of from about 60 to 200 psig for a period of at least about 1 hour.

* * * * *